(12) United States Patent
Hochstedler

(10) Patent No.: US 6,707,476 B1
(45) Date of Patent: Mar. 16, 2004

(54) AUTOMATIC LAYOUT SELECTION FOR INFORMATION MONITORING SYSTEM

(75) Inventor: R. Benjamin Hochstedler, Whitefish Bay, WI (US)

(73) Assignee: GE Medical Systems Information Technologies, Inc., Waukesha, WI (US)

(*) Notice: Subject to any disclaimer, the term of this patent is extended or adjusted under 35 U.S.C. 154(b) by 445 days.

(21) Appl. No.: 09/609,736

(22) Filed: Jul. 5, 2000

(51) Int. Cl.⁷ .................................................. G09G 5/00
(52) U.S. Cl. ........................ 345/789; 345/744; 345/797; 345/812; 345/846
(58) Field of Search ................................ 345/700, 789, 345/744, 745, 797, 812, 846

(56) References Cited

U.S. PATENT DOCUMENTS

| | | | |
|---|---|---|---|
| 5,473,536 A | | 12/1995 | Wimmer |
| 5,625,783 A | * | 4/1997 | Ezekiel et al. ............... 709/320 |
| 6,081,750 A | * | 6/2000 | Hoffberg et al. ............... 700/17 |
| 6,300,950 B1 | | 10/2001 | Clark et al. |
| 6,462,759 B1 | * | 10/2002 | Kurtzberg et al. ........... 345/803 |
| 6,473,752 B1 | * | 10/2002 | Fleming, III .................... 707/4 |
| 6,512,529 B1 | * | 1/2003 | Janssen et al. .............. 345/790 |

* cited by examiner

Primary Examiner—Kristine Kincaid
Assistant Examiner—Peng Ke
(74) Attorney, Agent, or Firm—Michael Best & Friedrich LLP

(57) ABSTRACT

A method of switching the layout of an information monitoring system. Layouts are sets of graphical components that are associated with monitored or sensed activities. The invention provides a mechanism for switching the layout when conditions of the monitoring system change. The system determines the currently used components for the current layout, determines the currently used capabilities of the system, and determines a correspondence between the set of currently used components and currently used capabilities. The system reviews a group of layouts and determines a correspondence between the components in the layouts, in the group of layouts, and the set of currently used capabilities of the system. A layout switch occurs if one of the layouts in the group of layouts more closely corresponds to the currently used capabilities of the system than the current layout.

38 Claims, 13 Drawing Sheets

Fig. 10

AUTOMATIC LAYOUT SELECTION FOR INFORMATION MONITORING SYSTEM

The present invention relates to methods and devices used to display information. More particularly, the invention relates to the display of information using configurable arrangements of interface components Patient monitors, computers, and similar devices present information on a monitoring device or monitor such as a CRT display, flat panel display, or similar device. The image displayed on the monitor is often incorporated in a graphical user interface ("GUI"), which may include one or more windows, icons, buttons, menus, and similar control elements that may be selected using a variety of mechanisms such as a pointing device or a stylus.

Generally, GUIs are made up of a set of components. A user-definable description of the set of components, the attributes of the components, and the arrangement of the components is referred to as a "layout." In patient monitoring applications, the components of a GUI often include parameter blocks, which display real-time information about patient vital signs and provide controls for adjusting the display of that information; waveform windows, which display vital sign waveforms in real time and provide controls for adjusting the display of the waveforms; control buttons assigned various functions; and case timers for timing activities. In many patient monitoring systems, GUIs are configured such that all components in a layout are displayed even if the function or activity associated with that component is not in use. For example, if a GUI is configured to display blood pressure, temperature, blood oxygen level, and an electrocardiogram ("ECG") waveform, but only blood pressure, blood oxygen level, and temperature are being monitored, the component associated with the ECG waveform is still displayed by the GUI (although the unused component is usually displayed in a disabled form).

The active components in a GUI change between phases of diagnoses and treatment. Changes are also likely to occur when there is a change in the care unit in which the patient is monitored, change in the type of care unit in which the monitoring system is used, change in the type of medical procedure being carried out, or other similar change. Further, different users (surgeons, anesthesiologists, general practitioners, nurses, etc.) often monitor different patient information. Thus, the active components in a GUI change frequently.

SUMMARY OF THE INVENTION

It would be preferable, if the layout of the GUI changed with the needs of users and the stage of medical treatment. However, present information monitoring systems that use configuration arrangements of interface components lack this capability. The invention provides a method and an apparatus for automating the change of the layout of a GUI for an information monitoring system. The system determines the active or currently used components of the current layout and monitors the system to detect changes in the system's capabilities (e.g., an additional sensor is added) or changes in the system's environment (e.g., a switch is made from one medical procedure to another). After detecting one or more changes in the system, the system reviews a group of available layouts and determines which, if any, more closely matches the system as changed. If an available layout more closely matches the changed system, then the system may implement an automatic change or switch of the layout or prompt the user to change the layout by presenting a selection of layout options. Alternatively, the system may do nothing upon the occurrence of a change or it may check a system threshold. If the system is configured to check the threshold, it will not implement a layout switch until the threshold is exceeded by a value based upon the correspondence between the changed system and one of the available layouts.

A layout change can encompass a change of an overall layout (a layout with multiple, and usually different components), a change of a sub-layout (a more specialized version of an overall layout), a change of a waveform window (a component designed to illustrate waveforms), or a change of a parameter block (a component designed to show non-waveform information).

As is apparent from the above, it is an advantage of the present invention to provide a method and system of changing or switching the layout in an information monitoring system. Other features and advantages of the present invention will become apparent by consideration of the detailed description and accompanying drawings.

BRIEF DESCRIPTION OF THE DRAWINGS

In the drawings:

FIG. 10 is an illustration of the layout shown in FIG. 2 with a dialog box of proposed selections for changing a waveform window layout.

DETAILED DESCRIPTION

Figure 1:
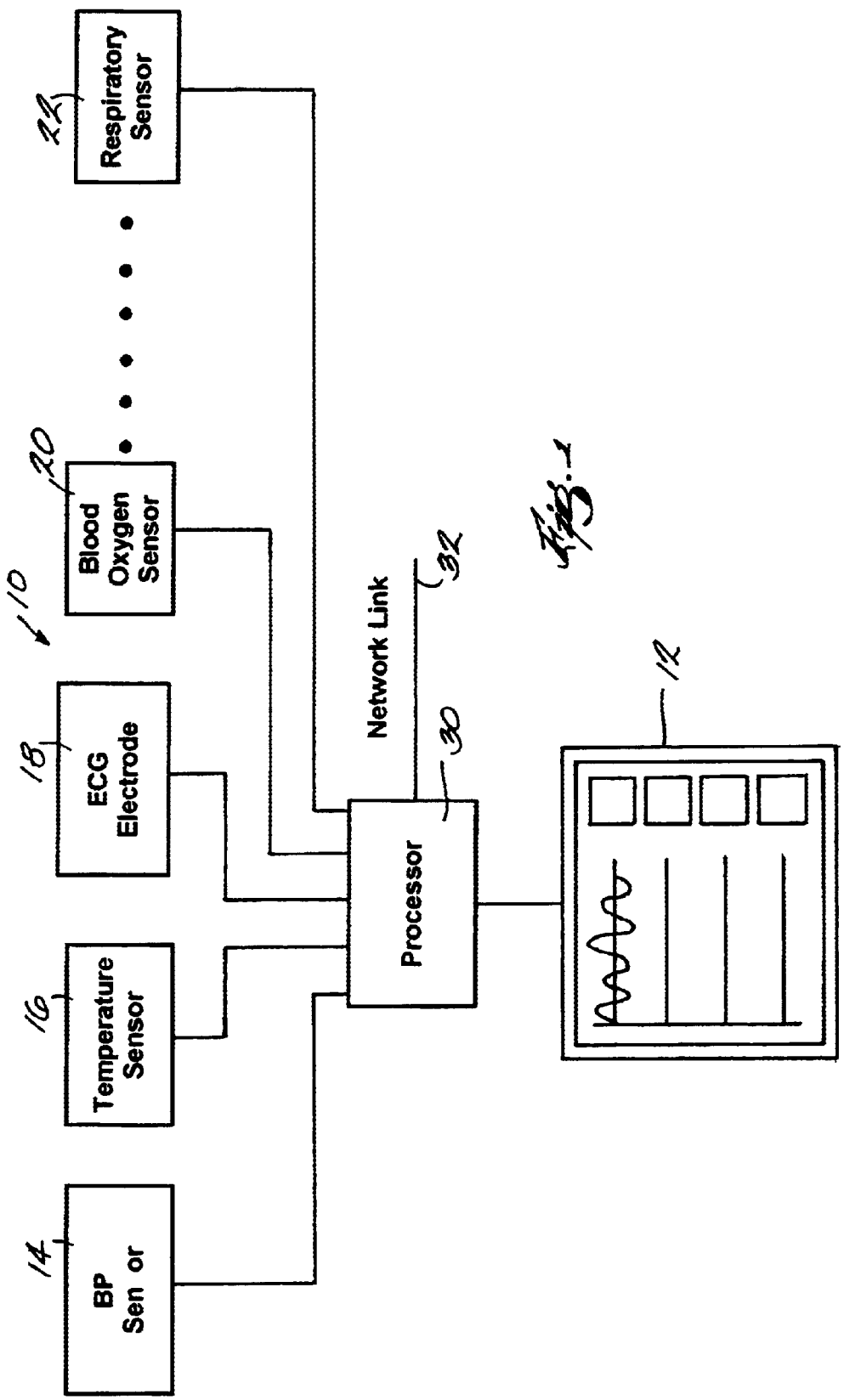
FIG. 1 is a schematic diagram of a patient monitoring system.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

FIG. 1 illustrates a patient monitoring system 10 that displays information on a monitoring device or monitor 12. The system 10 represents an exemplary system whereby various types of information may be displayed depending on the capabilities of the system that are utilized at any particular time. Of course, other types of information monitoring systems, such as systems designed to monitor a device, animal, or other entity are encompassed by the invention.

The system 10 includes a plurality of sensors, including a blood-pressure sensor 14, a temperature sensor 16, an ECG electrode 18, a blood oxygen sensor 20, and a respiratory sensor 22. Other sensors could be added to the system or the sensors shown could be removed from the system. The type of sensor used will depend on the type of activity monitored. Each of the sensors outputs data signals that are delivered to a processor 30. The processor 30 processes the signals from the sensors using algorithms known in the art and generates a graphical display on the monitor 12. The processor 30 may also receive information from other sources, such as a second patient, through a network link 32.

Figure 2:
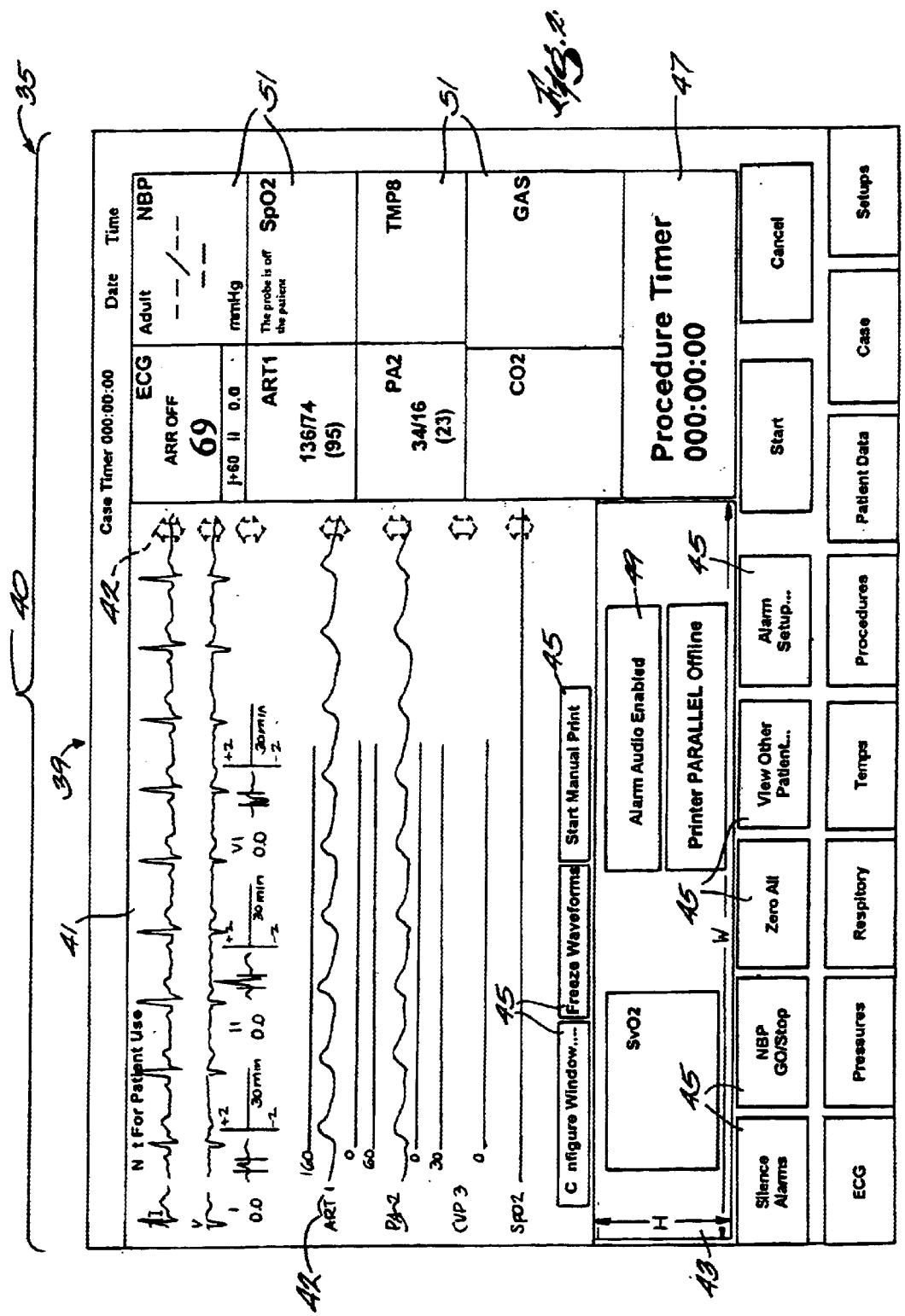
FIG. 2 is an illustration of an exemplary layout displayed on a monitor of the patient monitoring system shown in FIG. 1.

As best seen by reference to FIG. 2, the information from the sensors 14–22 is displayed in a graphical user interface ("GUI") 35. The GUI 35 includes a number of components that are used to build or construct a layout 39. In general terms, a layout is just a configuration of components, but as used herein a layout will generally refer to the entire group of components displayed on a monitor to display monitored activity. A layout does not include components that are part of the base operating system GUI. As shown in FIG. 2, the layout 39 has a bed layout 40 (which is simply a layout that contains other components.) The components inside the bed layout 40 include a waveform window 41, controls 42 for the waveform window 41, sub-layouts 43, command buttons 45, a procedure timer 47, message windows 49, and parameter blocks 51.

The number and type of sensors used in the system 10 changes based on the type of information that an end user desires to see. Thus, additional sensors may be added to the system, sensors may be removed from the system, or sensors may be deactivated based on the desires of the user. The number and type of active sensors determines the capabilities of the system 10. As should be apparent, if the system 10 is configured without a blood pressure sensor, it lacks the capability to measure blood pressure. In addition, if the system is configured with a blood pressure sensor, but the sensor is deactivated, the system 10 is treated as lacking the capability to measure blood pressure. These same rules apply to other types of sensors.

How the system 10 displays information may be modified through the controls 42 and buttons 45 that are associated with the layout 39. The controls 42 and control buttons 45 provide an end user a mechanism for adjusting the display of information to suit that user's preferences or needs. For example, using the controls 42 a user may adjust the location of a waveform as well as the height of the waveform. Preferably, the components of the GUI are also created with standard windowing-type controls that allow modification of the size and location of components. With the control buttons 45, the user may configure a waveform window such as by adjusting the rate at which the waveform travels across the screen, freeze a waveform or other parameter reading, print a waveform, zero parameter readings, silence active alarms, view information from other sources through the network link 32, or adjust alarm settings.

As noted above, each layout 39 may be treated as a user-definable description of the set of components, the attributes of the components, and the arrangement of the components of the GUI 35. Each sub-layout 43 has a width W and a height H. In the embodiment described herein, the height and width of any sub-layout 43 that will be swapped or switched for an existing sub-layout must match the height and width of that existing sub-layout. Unlike a bed layout, a sub-layout may not contain another sub-layout.

Each waveform window 41 has a waveform window layout (the relationship of how waveforms are displayed in a waveform window). Any waveform window layout may apply to any waveform window regardless of the size of the waveform window or its placement within the containing bed layout or, if applicable, the containing sub-layout. Waveform windows 41 are used to display information that is best represented in a time-changing waveform, such as ECG information and respiratory information.

Each layout 39 may contain any number of waveform windows 41 or sub-layouts 43. A list of layouts is referred to as a "layout group." Generally, a layout group contains a homogenous cluster of layouts. That is, if a layout group contains bed layouts, it contains only bed layouts. Likewise, a layout group could consist of a list of waveform window layouts.

Figure 3:
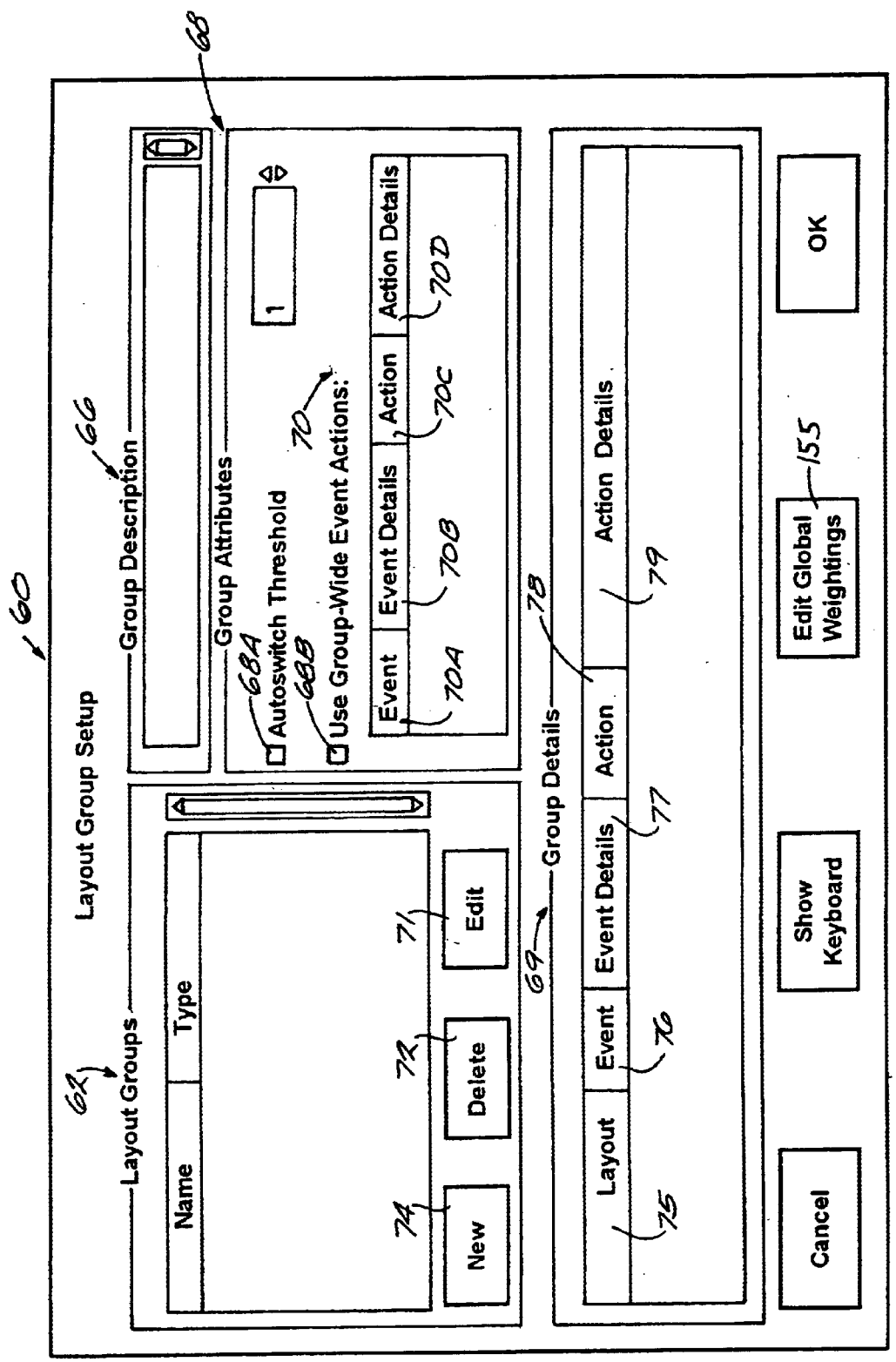
FIG. 3 is an illustration of a layout group setup dialog box.

Layout groups are defined using a layout groups setup window or dialog box 60 (FIG. 3). The dialog box 60 provides mechanisms to allow a user to browse, view, edit, and define layout groups. The dialog box 60 includes a layout groups window 62 with a scroll bar 64. The layout groups window 62 displays defined layout groups for the system 10. When a user selects a particular group by clicking or pressing on its name, the details of that group are displayed in a group description window 66, an attributes window 68 having an auto switch button 68A and a use group-wide event actions button 68B, and a group details table or window 69.

The group attributes window 68 includes a group-wide event actions table 70 with an event column 70A, an event details column 70B, an action column 70C, and an actions detail column 70D. A user may edit the currently displayed layout group by selecting an edit button 71. Once the user presses the edit button 71, the name, group details, group description, and description of the layout group may be changed. The layout group type may not be changed.

The dialog box 60 also includes a delete button 72 and a new button 74. If a user selects the delete button 72, the system 10 prompts the user for confirmation to delete the currently selected layout group. The system 10 then deletes the selected layout group. If the user presses the new button 74, the system waits for the user to enter information concerning the new layout group. The information required by the system 10 includes the type of layouts in the group (bed layouts, waveform window layouts, or sub-layouts). Once this information is entered, the system 10 then creates a new unnamed group and enters the edit mode to allow the user to make any necessary modifications, including naming the group.

Figure 4:
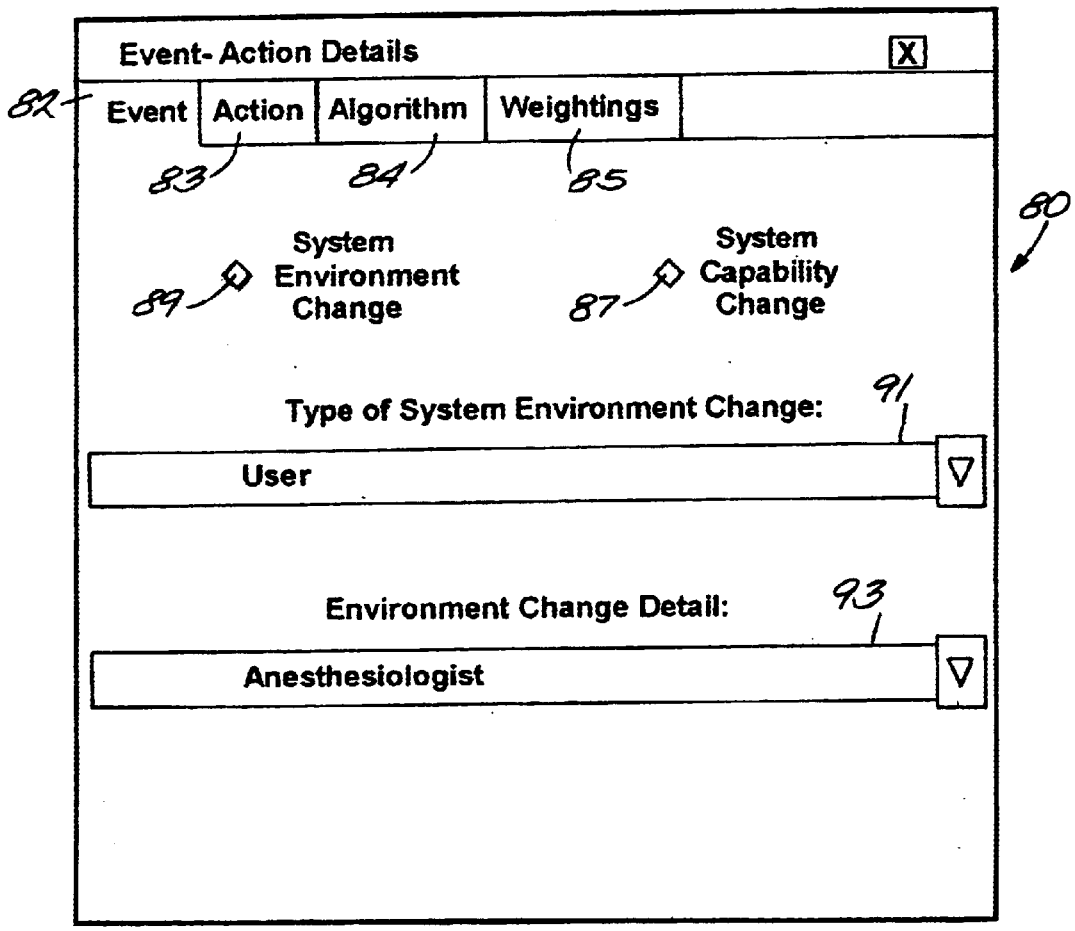
FIG. 4 is an illustration of an action details dialog box where an event tab has been selected.

The dialog box 60 is designed to permit a user to add or edit an entry in the group details window 69 by selecting a row in the group details window. Selecting a row causes the system to display a summary (not shown) of the settings for the selected entry. The group details window includes additional features in the form of a layout column 75, an event column 76, an event details column 77, an action column 78, and an action details column 79. When a new row in the layout column of the group details window is selected, the system 10 adds a new layout to the active layout group. Once the user has selected a layout, an event—action details dialog box 80 (FIG. 4) is displayed by the system 10. If the user has selected a row from the group-wide event actions table 70 an event action details dialog box (not shown) is also displayed.

A bed layout and the layouts of the waveform windows and the sub-layouts contained within that bed layout are referred to as a "layout set." A layout set is valid only if it can be rendered on the display 12. Therefore, a layout set always has one bed layout, and can contain any number of waveform windows and sub-layouts. How well the overall layout matches the current capabilities of the system 10 depends on the combined set of waveform window layouts and sub-layouts contained within the overall layout's bed layout.

To help ensure that the layout 39 of the GUI 35 matches the capabilities of the system, the system 10 is designed such that a user may pre-program the manner in which the system 10 responds to a change in the capabilities or environment of the system. For the system described herein, there are two categories or types of changes that may occur. A first type of change or state relates to a change in the capabilities of the system (e.g., a blood oxygen sensor is added). In the first state, the layout is modified so that information associated with the added or subtracted capability is displayed in the GUI. A second type of change or state relates to a change in the system environment (such as a change of user, change in the phase of the case, change in the care unit in which the patient is monitored, change in the type of care unit in which the system 10 is used, change in the type of medical procedure being carried out, or other similar change). In the second state, the layout is modified according to user specific desires.

When configuring the system 10, the user may specify that the system 10 does nothing in response to a system change (which is a default setting and referred to herein as Option 1). The user may also specify that the system specify an automatic layout switch (Option 2), or the user may specify that an automatic layout switch occur after prompting the user for approval of the proposed change (Option 3). Lastly, the system may provide a list of layouts (or as noted above a "layout group") from which the user may choose, along with a preview of what the display will look like once it has changed for each layout in the list of layouts (Option 4).

For Options 2–4, the user defines a list (or layout group) of possible layouts to which to switch for a particular type of system change. The layout group is the entire list of layouts of a particular type defined on the system so that when a new layout is created, it can automatically be switched to without having to add the new layout to existing layout groups. The user may further define the behavior of Options 2–4 by specifying that a "best guess" algorithm be applied to the layout groups when a change in the capabilities of the system occurs. That is, the best guess algorithm may be applied when there is a first state change. For Options 2 and 3, the system uses the best guess algorithm to pick or select one layout from the layout group that most closely matches the current or active capabilities of the system 10. For Option 4, the system uses the best guess algorithm to rank the possible layout sets in order of the best fit to the worst fit for the current set of system capabilities.

When Option 3 is used, the user has the choice to cancel the layout switch, perform the layout switch, or pick an alternate layout set. When the user picks an alternate set, the system operates as if it were configured to perform Option 4.

Referring back to FIG. 4, the event—action details dialog box 80 provides mechanisms for a user to define the details of the action to be taken when a particular event happens on the system 10. An action is defined for all of the layouts in a layout group when that action is listed in the group-wide event actions table 70. When defined in the group details table 69, the action is defined for an event that occurs only when the specified layout is active. A particular layout may be specified to be in more than one layout group. However, the action to be taken for a particular event for a layout may only be defined once.

The event-action details dialog box 80 includes four tabs 82, 83, 84 and 85 corresponding to options for four areas: events, actions, algorithms, and weightings. (Events, actions, algorithms, and weightings are discussed in greater detail below.) Under the event tab 82, a user may specify whether the layout will respond to a change in the system's capability or environment using a capability button 87 and an environment button 89. If the capability button is 87 selected, no further adjustments to the system may be made. If the environment button 89 is selected, the system 10 waits for additional data input through a type-of-change-dialog box 91 and a change detail dialog box 93. In this manner, the system prompts the user to specify the type of environment change and the specific instance of that environment type. For instance, in the exemplary event action details dialog box shown, the event specified is a change of the type of "user" to an "anesthesiologist."

Figure 5:
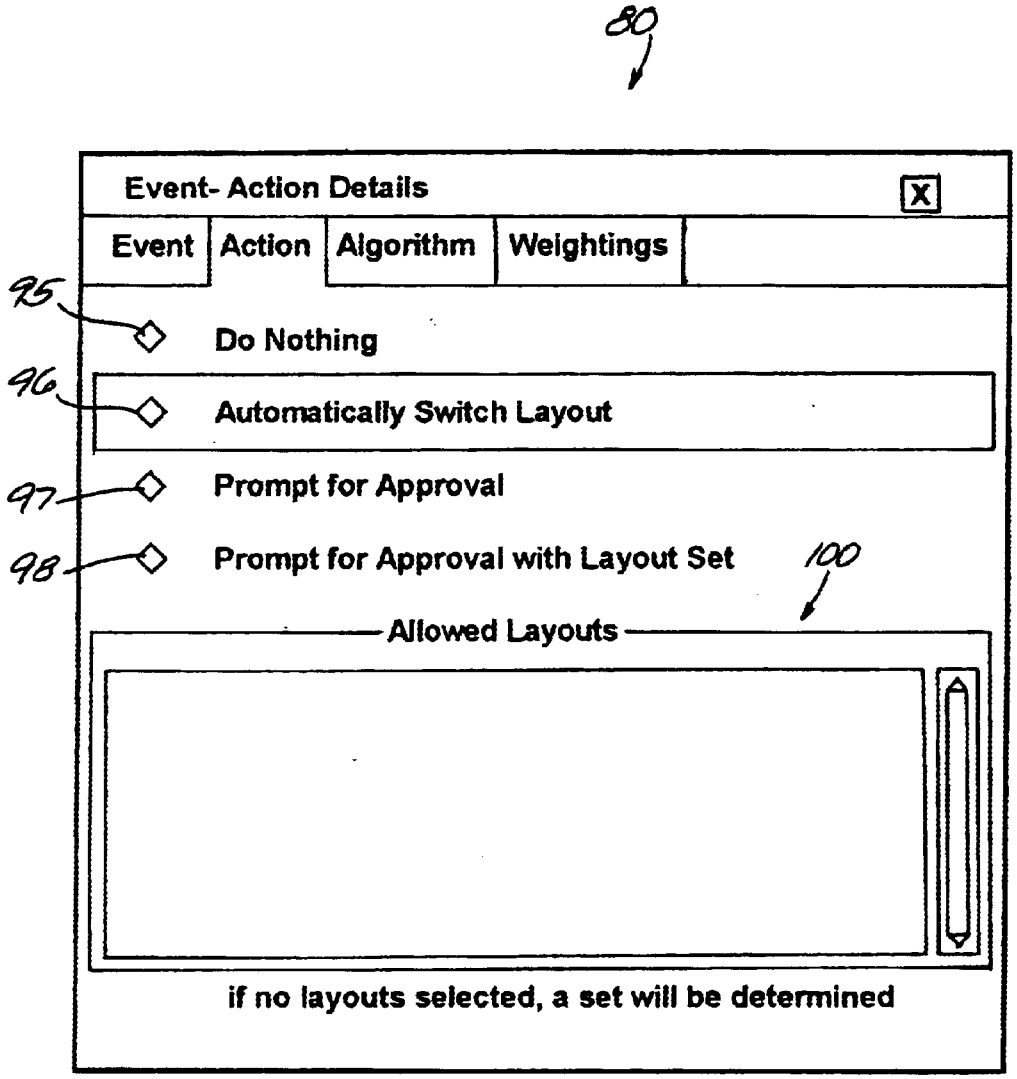
FIG. 5 is an illustration of the action details dialog box of FIG. 4 where an action tab has been selected.

As shown in FIG. 5, the action tab 83 provides mechanisms to permit a user to select one of four action or option buttons 95, 96, 97, and 98. (The options correspond to the Options 1–4 defined above.) If a button besides the "do nothing" button 95 is selected, then the user may specify the layouts that may be switched to. The system 10 displays the list of layouts with types that match the selected option in an allowed layouts window 100. The user may then choose from the list of displayed layouts in the allowed layouts window 100 by selecting the desired layouts. If the user does not select at least one layout after selecting buttons 96, 97 or 98, the system 10 automatically generates a layout set using one of the specified algorithms corresponding to the relevant action or event. When the user configures a group-wide event action, an extra option is available: a use group-wide action button (not shown) is displayed by the system.

Figure 6:
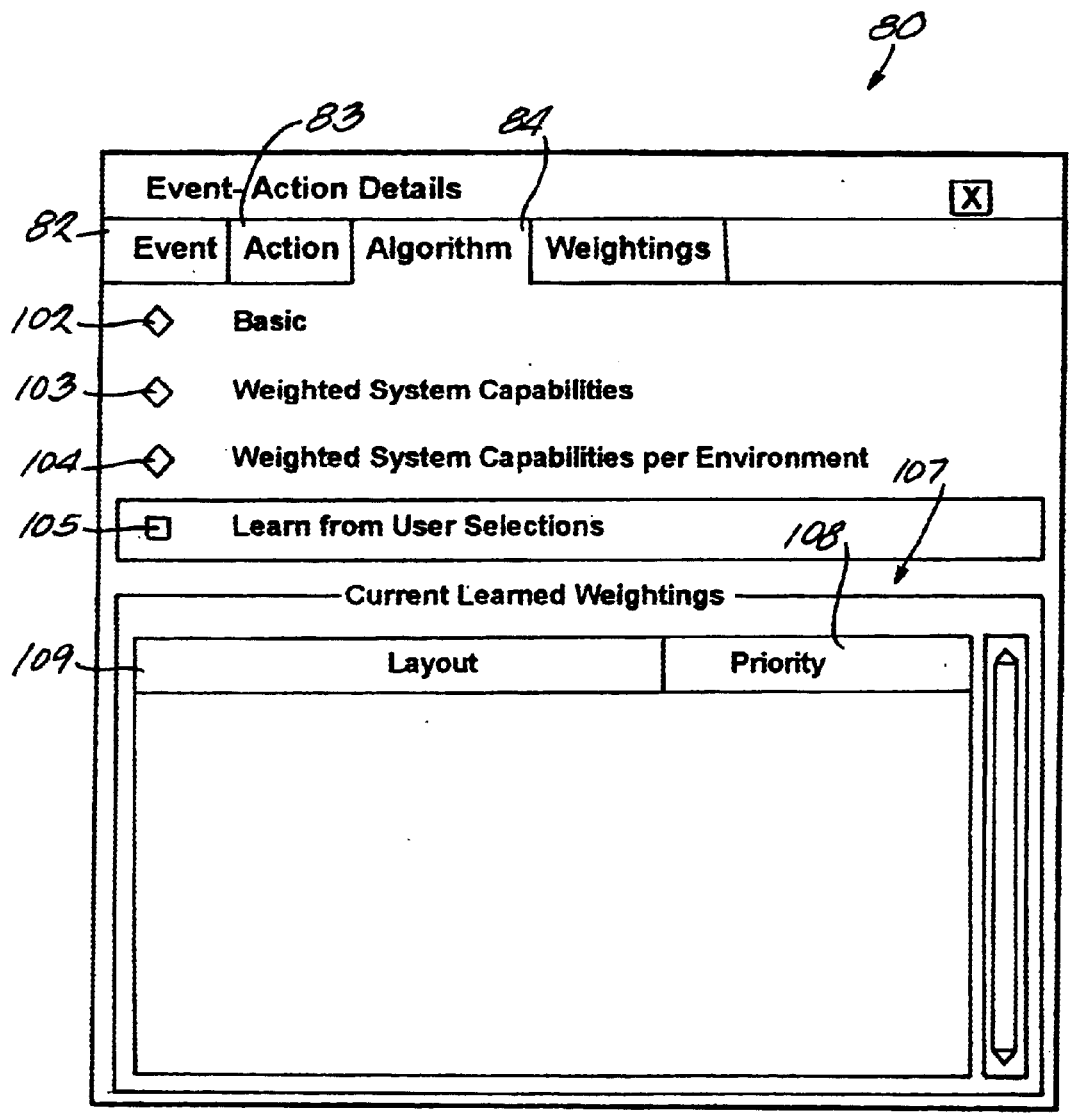
FIG. 6 is an illustration of the action details dialog box of FIG. 4 where an algorithm tab has been selected.

As shown in FIG. 6, the algorithm tab 84 provides a mechanism to permit a user to select the algorithm implemented by the system 10 to switch a layout upon the occurrence of an event. The algorithm tab includes four algorithm buttons 102, 103, 104, and 105 and a current learned weights window 107 with a priority column 108 and a layout column 109. Provided the user has selected an action with the mechanisms provided by the action tab 83, the algorithm buttons 102–105 are enabled by the system 10, and those buttons may be used by the user to make an algorithm selection.

The basic best guess algorithm (which is activated by selecting button 102) determines the correspondence between components in a presently used layout and the active capabilities of the system 10. The algorithm assigns a perfect score to a layout set that monitors exactly the parameters monitored by the system. If the layout set contains extra parameters, the layout set is given a lesser score than that which matches perfectly, but it is given a higher score than any layout set that is missing parameters. Each parameter is considered equal to all other parameters. However, the best guess algorithm does not consider command buttons, message windows, or procedure timers.

The weighted system algorithm is activated by selecting button 103. This algorithm builds on top of the best guess algorithm by assigning certain user-definable weights to certain parameters and/or GUI components. GUI components or parameters that match the capabilities of the system 10 are multiplied by the weight. Missing components are not weighted. The layout with the highest weighted score is considered to have the highest correspondence with the system and, thus, chosen for use in the GUI. A variation of the weighted system algorithm is a weighted system capabilities per environment algorithm. This algorithm is activated by selecting button 104. In the weighted system capabilities per environment algorithm, each particular parameter and GUI component is weighted differently for different states of a particular environmental aspect. For instance, it might be important for a procedure timer to be on the display for use in the operating room, but in the ICU, it can be more important for a message window to be displayed. Thus, these parameters will be given different weights depending upon the environment (e.g., an operating room or an ICU) in which the monitoring is occurring. Finally, an artificial intelligence or learning algorithm may be used where the system 10 builds its own weights for layout sets for particular system configurations and environmental states. This algorithm can be activated by selecting the button 105. In the learning algorithm, when a layout set is switched automatically, and the user doesn't change the layout switch, the system gives that layout set a greater weighting in the future. If the user changes the layout soon after the auto switching is performed, then that layout set is given a negative weighting for the current system configuration. When the user is given a list of layout sets from which to choose, the set chosen is given a higher weighting in the future unless the user changes the layout set soon after. The learning algorithm can be used in conjunction with any of the first three algorithms. If the user has selected the learning algorithm by selecting the learn from user selections button 105, and the system 10 has performed an automatic layout switch because of a specific event, then the layouts that were switched to and their priorities are listed under a second weightings tab or a different dialog box (not shown).

Figure 7:
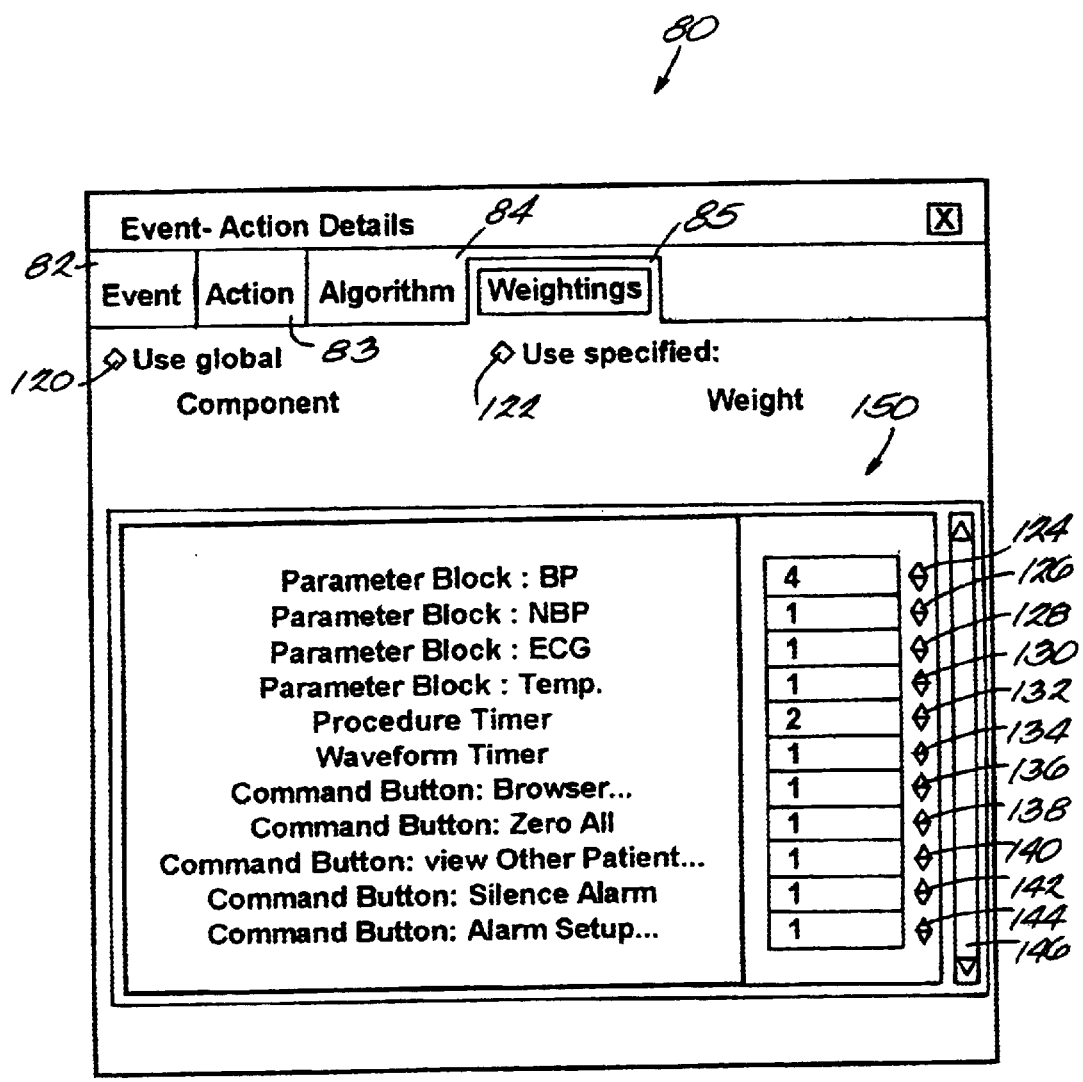
FIG. 7 is an illustration of the action details dialog box of FIG. 4 where a weightings tab has been selected.

The weights of the GUI components for the event being configured may be assigned by the user using the mechanisms provided under the weightings tab 85, as best seen in FIG. 7. The system 10 permits the weightings to be specified provided the user did not select use group-wide event action button 68B in the attributes window 68. The weightings tab includes a use global button 120 and a use specified button 122. If the user selects the global button 120, then the global weightings for the event are displayed and the user may change them using input mechanisms 124–146 in a weightings window 150. If the user selects the use specified button 122, then the global setting for the subject event is copied and displayed in the weightings window 150. Any changes made to the weights in the window do not affect the global settings for that event.

While the weightings tab 85 provides a mechanism to adjust the weightings of components, the system 10 does not permit a user to remove any of the components from the selected layout using the weightings tab. If no global or group-wide weights have been assigned for the particular event being configured, the system 10 assigns default weights of "1" to every component in the layout. The user may then specify or adjust each component's weight. Global weighting may also be adjusted using an edit global weights button 155 in the dialog box 60 (FIG. 3). When the user selects the edit global weightings button 155, the system 10 displays an adjusted weightings dialog box (not shown) that is similar to the event-actions dialog box 80, but lacking action and algorithm tabs. The adjusted weightings dialog box provides mechanisms to adjust component weightings Another feature of the invention relates to a user-specified threshold for switching layouts. A user may specify a system-wide threshold. The system 10 may then compare that threshold to the score for the current layout set generated by the presently used layout switch algorithm (which may be one of the above algorithms). If the threshold is not exceeded, the system does not switch the layout or prompt the user to change the layout, even if there is a layout in a layout group that more closely matches or corresponds to the current capabilities of the system 10. The user may set the threshold such that no switching will occur if the current layout set contains all of the parameters needed for the current set of system capabilities, but as soon as the current layout set is missing one, the system will make a layout switch using one of the layout switch algorithms.

FIGS. 8 through 13 illustrate the end results of implementing the algorithms discussed above. In particular, the drawings illustrate changes or layout switches from the layout shown in FIG. 2 to various other layouts.

Figure 8:
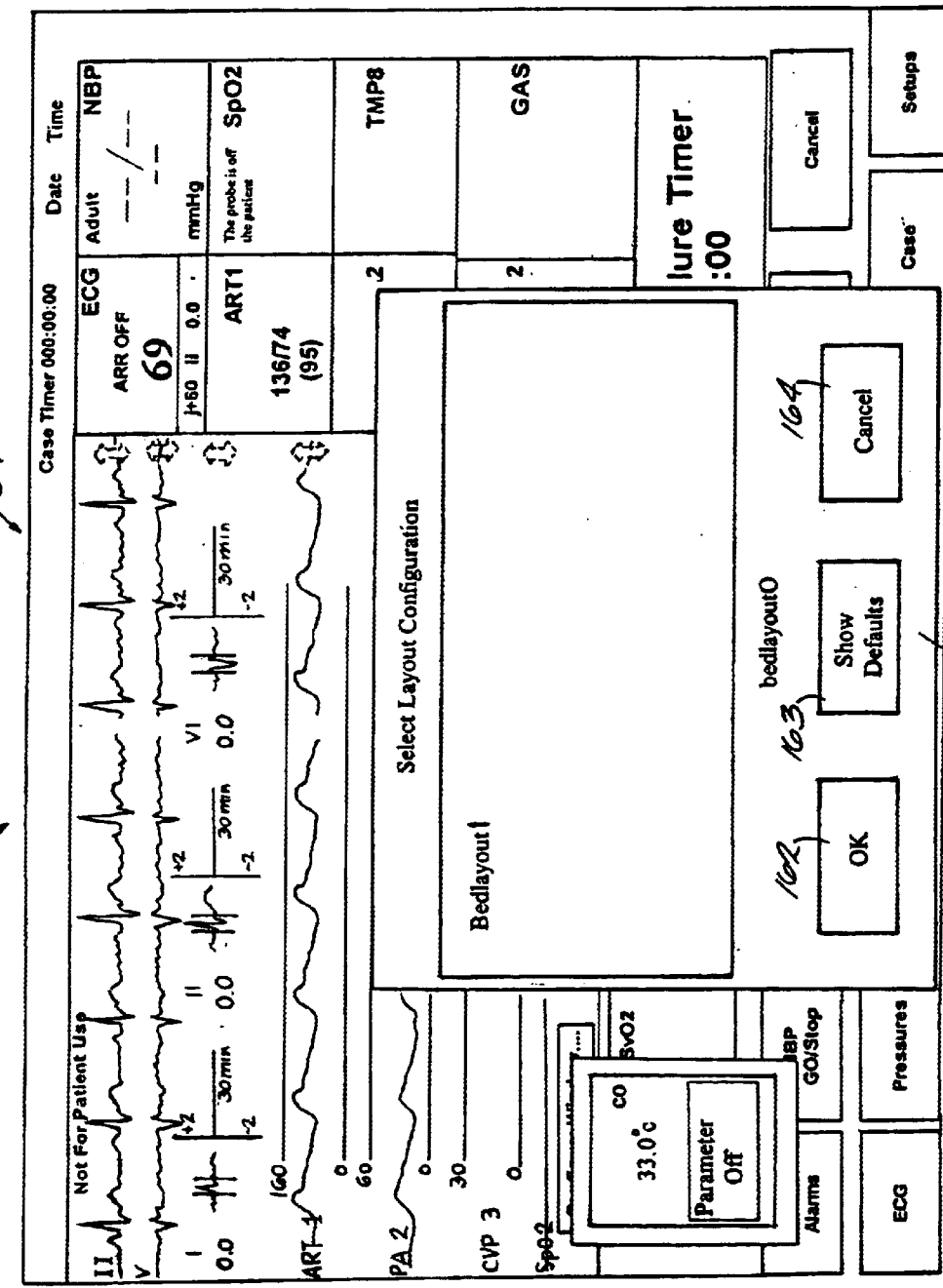
FIG. 8 is an illustration of the layout shown in FIG. 2 with a dialog box of proposed selections for switching the existing layout to a second layout.
Figure 9:
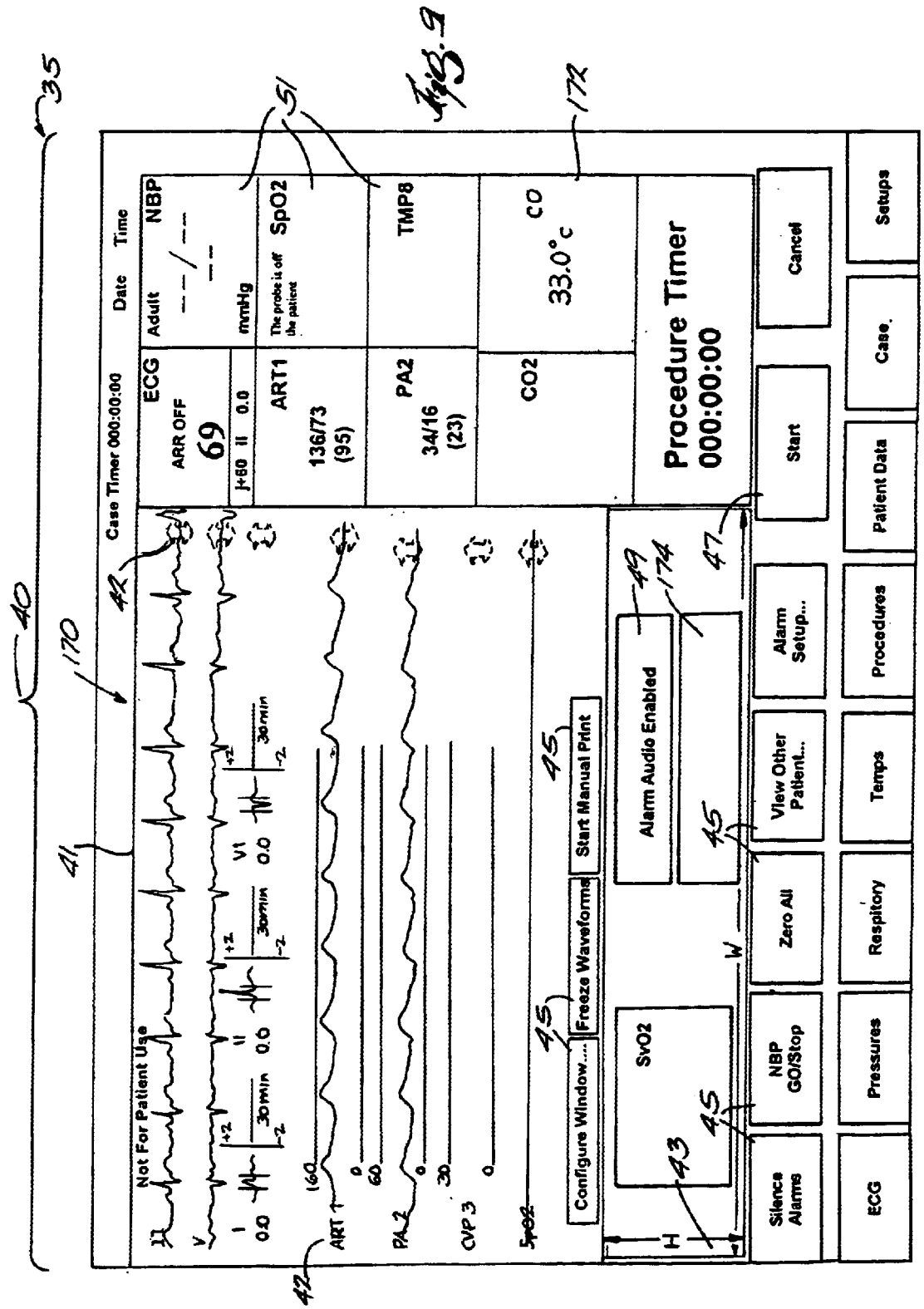
FIG. 9 is an illustration of the second layout displayed on the monitor of the patient monitoring system once a selection from the dialog box shown in FIG. 8 has been made.
Figure 11:
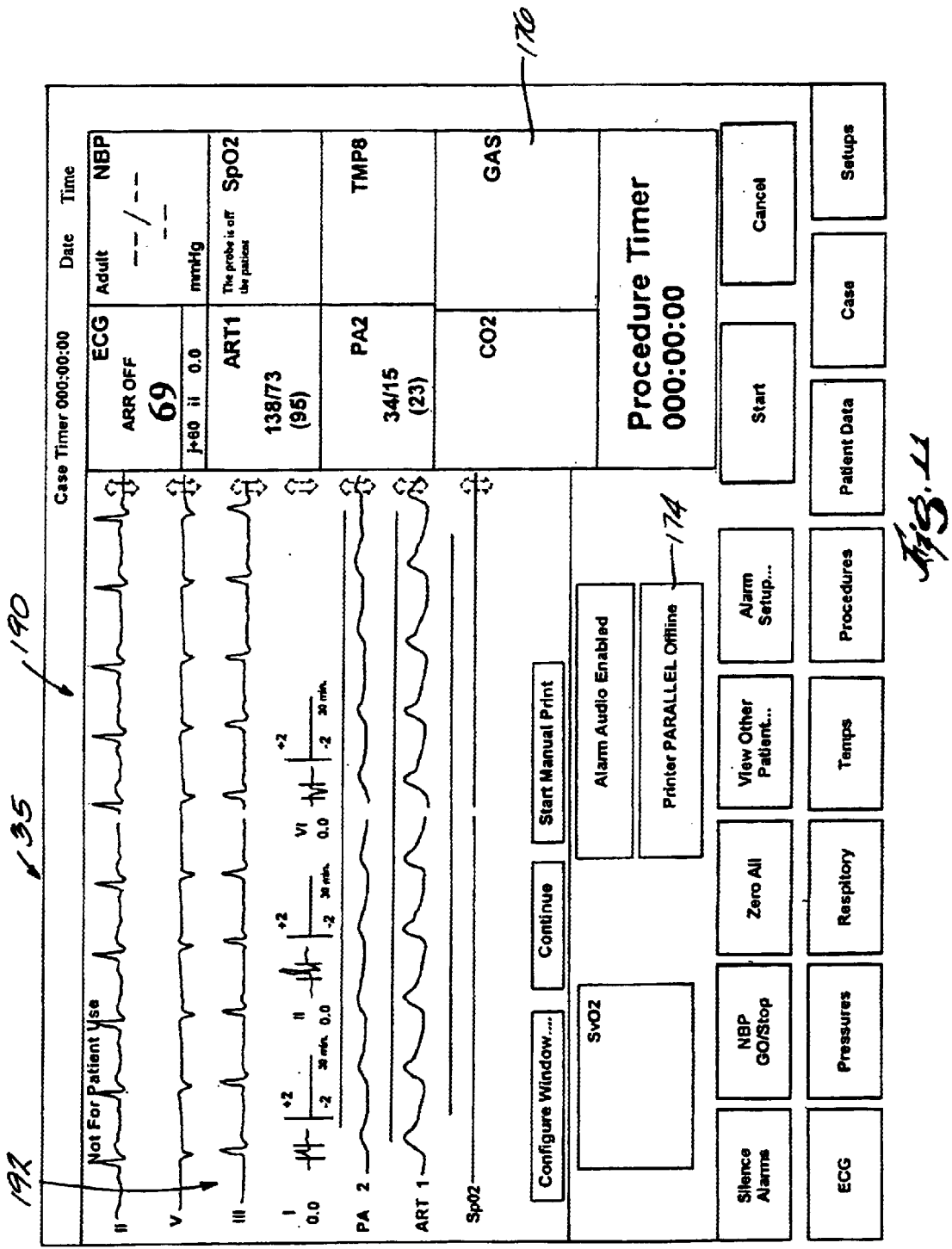
FIG. 11 is an illustration of a third layout which is displayed on the monitor of the patient monitoring system once a selection from the dialog box shown in FIG. 10 has been made.

FIG. 8 illustrates an implementation of Option 3 where a pop-up list or dialog box 160 is presented to the user showing the user that the overall layout is about to be changed to a new bed layout, Bedlayout1. Generically, the layouts listed in the dialog box 160 and other choices listed in the dialog boxes discussed below are referred to as "selections." The dialog box 160 includes an accept mechanism in the form of an OK button 162 to confirm the switch, a default selection button 163, and a CANCEL button 164 to cancel the layout switch. If the user selects the OK button 162, the layout is switched to a layout 170 shown in FIG. 9. The layout 170 contains a different parameter block 172 and contains a different message window 174.

Figure 10:
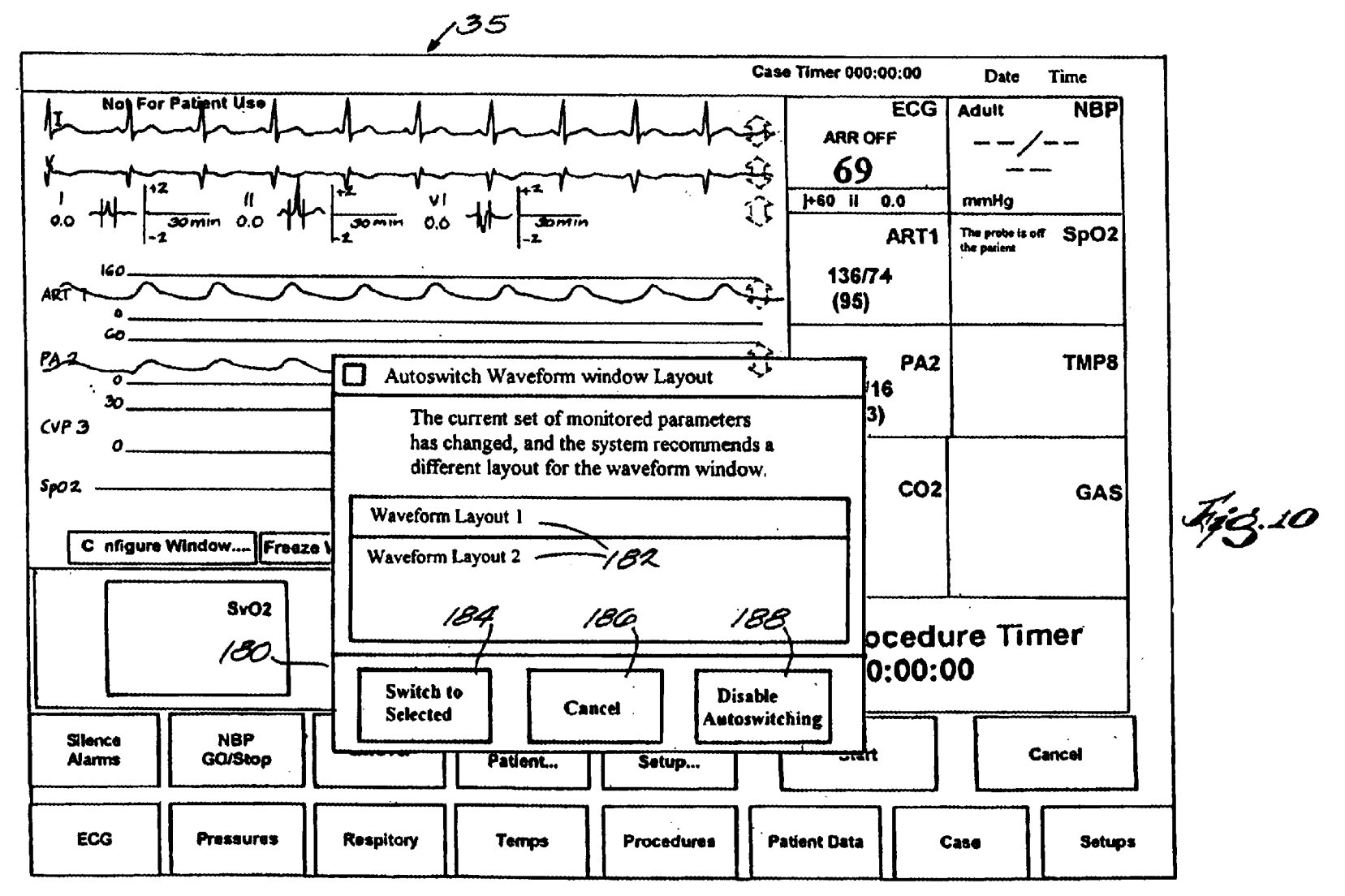

FIG. 10 illustrates the process by which a waveform window layout may be switched. If the system 10 detects a parameter switch or change in system capabilities that impacts information displayed as a waveform, the system 10 generates a waveform dialog box 180 with a list of one or more preferred waveform layouts 182. The dialog box 180 includes an OK or SWITCH TO SELECTED button 184, a CANCEL button 186, and a DISABLE AUTOSWITCHING button 188. If the user selects the SWITCH TO SELECTED button 184, a waveform window 190 (FIG. 11) replaces the waveform window 41. The waveform window 190 includes an additional waveform display 192, which corresponds to an additional ECG lead (III).

Figure 12:
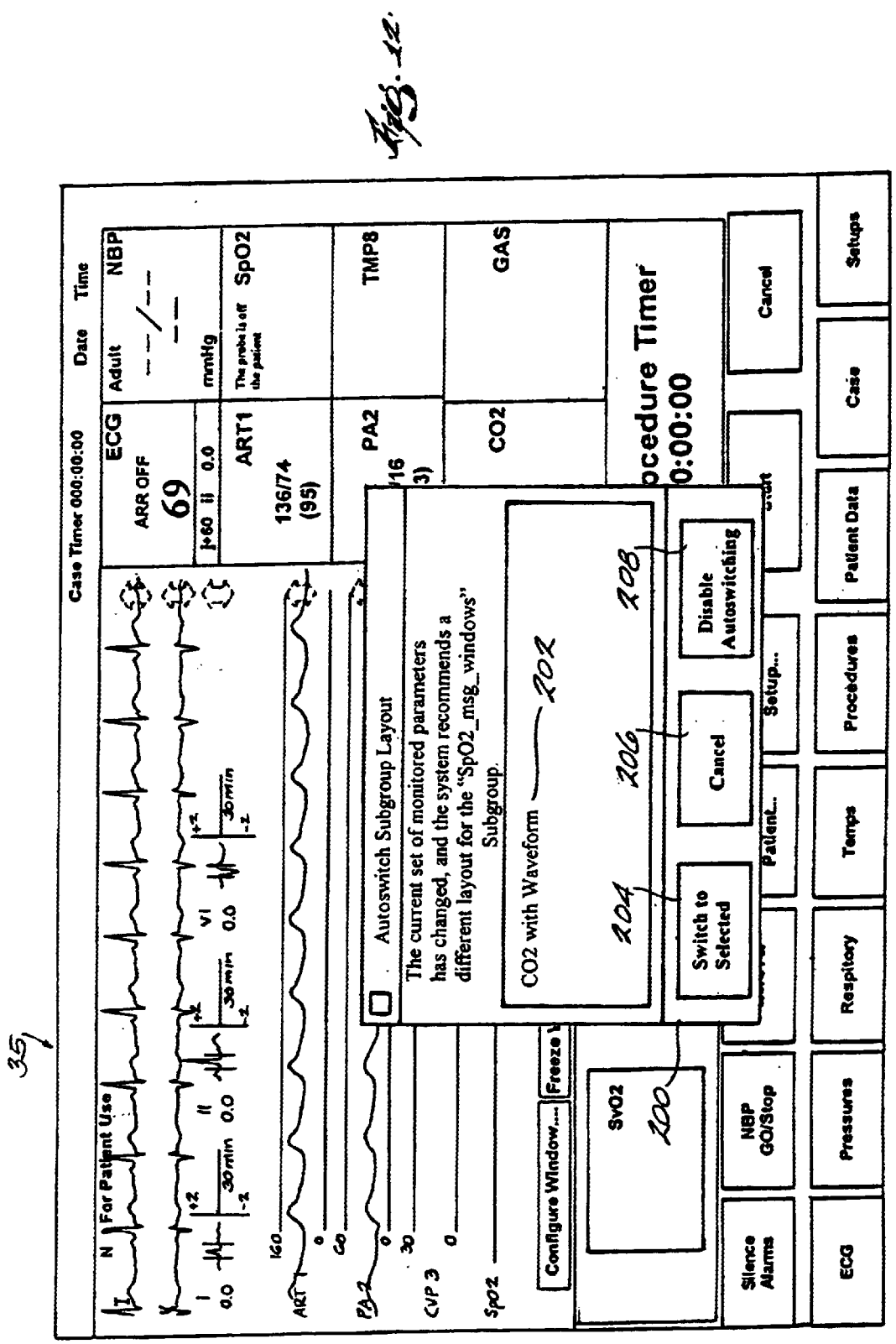
FIG. 12 is an illustration of the layout shown in FIG. 2 with a dialog box of proposed selections for changing a subgroup or sub-layout.
Figure 13:
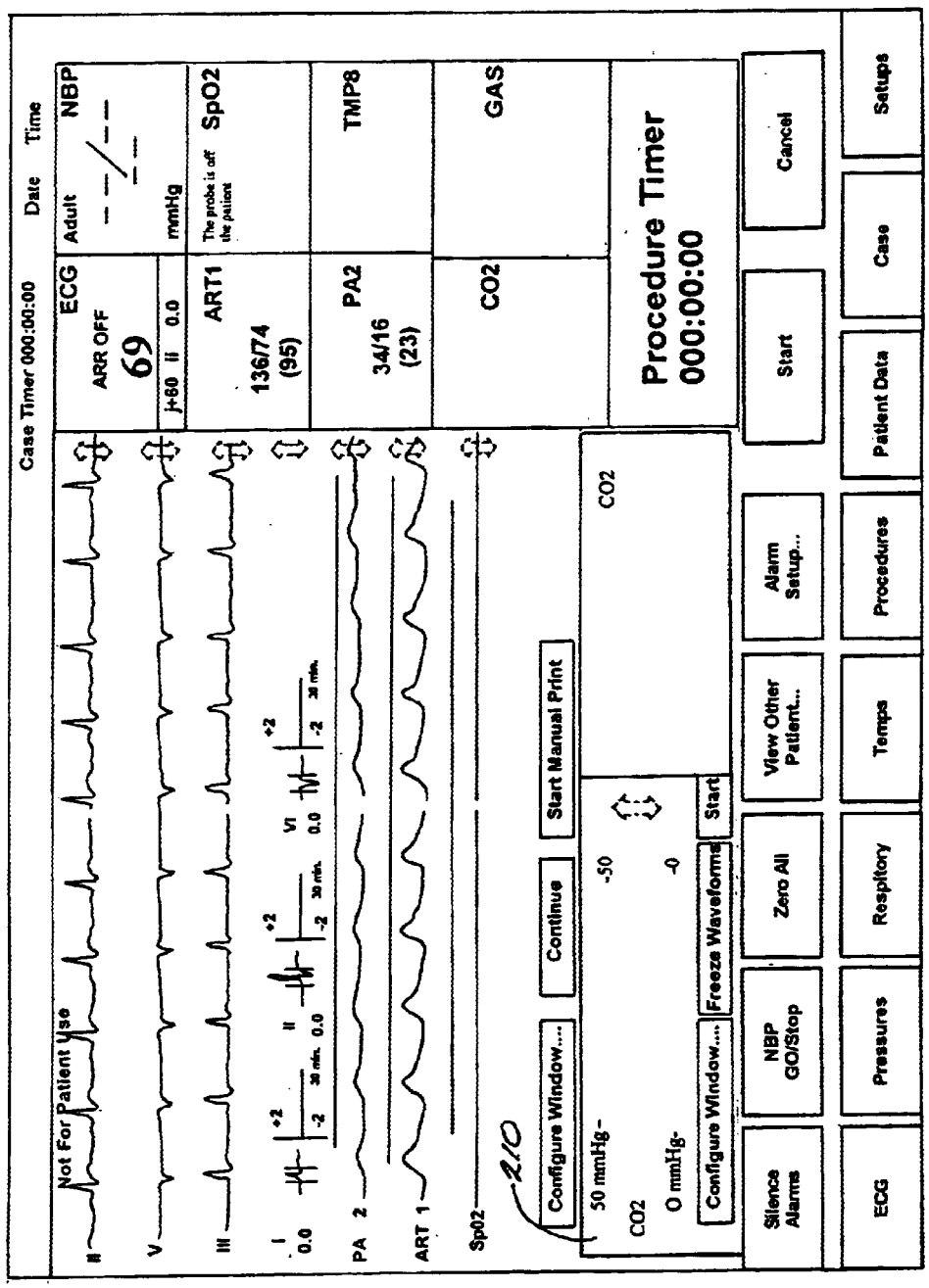
FIG. 13 is an illustration of a fourth layout which is displayed on the monitor of the patient monitoring system once a selection from the dialog box shown in FIG. 12 has been made.

FIG. 12 illustrates the process by which a sub-layout may be switched. If the system 10 detects a parameter switch involving information displayed in a sub-layout, the system 10 generates a sub-layout dialog box 200 with a list of one or more preferred sub-layout configurations 202. The dialog box 200 includes an OK or SWITCH TO SELECTED button 204, a CANCEL button 206, and a DISABLE AUTO SWITCHING button 208. If the user selects the SWITCH TO SELECTED button 204, the sub layout 43 is replaced by a sub layout 210 (FIG. 13).

As can be seen from the above, the invention provides a method and system for switching a layout of an information monitoring system. The invention also provides a method and system for switching components of a layout of an information monitoring system.

Various features and advantages of the invention are set forth in the following claims.

What is claimed is:

1. A method of switching the layout of an information monitoring system, the method comprising:

Determining a set of currently used components for a first layout;

Determining a set of currently used external information source monitoring capabilities of the system;

Determining a correspondence between the set of currently used components and the set of currently used capabilities;

Monitoring the system to detect one or more changes in the system's ability to monitor external source of information;

After detecting one or more changes in the systems reviewing a predetermined group of layouts and determining a correspondence between the components of at least one layout of the group of layouts and the set of currently used capabilities of the system; and Switching from the first layout to the at least one layout if the correspondence between the components of the at least on layout of the group of layouts and the set of currently used capabilities is greater than the correspondence between the set of currently used components and the set of currently used capabilities.

2. A method as claimed in claim 1, wherein the act of determining correspondence between components of at least one layout of the group of layouts and the set of currently used capabilities of the system includes implementing a best guess algorithm.

3. A method as claimed in claim 2, wherein a high score is assigned to a layout that exactly matches the set of currently used capabilities of the system.

4. A method as claimed in claim 2, wherein a layout containing more parameters than the parameters associated with the capabilities of the system is assigned a score that is higher than a layout with less parameters than the parameters associated with the set of currently used capabilities of the system.

5. A method as claimed in claim 1, wherein the act of determining a correspondence between components of at least one layout of the group of layouts and the set of currently used capabilities of the system is implemented using a weighted system algorithm.

6. A method as claimed in claim 5, wherein predetermined weights are assigned to layout components.

7. A method as claimed in claim 6, wherein layouts are assigned weighted scores based on the weights assigned to their components.

8. A method as claimed in claim 7, wherein the at least one layout is a layout with the highest weighted score.

9. A method as claimed in claim 7, further comprising defining a layout switch threshold.

10. A method as claimed in claim 9, further comprising comparing the layout switch threshold to a weighted score of a chosen layout.

11. A method as claimed in claim 10, wherein layout switching is prevented if the weighted score of the chosen layout is less than the layout switch threshold.

12. A method as claimed in claim 1, wherein the act of determining correspondence between components of at least one layout of the group of layouts and the set of currently used capabilities of the system includes building weights for layouts according to particular system capability and environmental states.

13. A method of switching layouts in a monitoring system, each layout having one or more components, the method comprising:

determining a set of currently used components for a first layout;

monitoring the system to detect one or more changes in the system's ability to monitor external sources of information;

after detecting one or more changes in the system, reviewing a predetermined group of layouts and determining a correspondence between the components of at least one layout of the group of layouts and a set of currently used capabilities of the system; and providing a switch option interface if the correspondence between the components of the at least one layout of the group of layouts and the set of currently used capabilities is greater than the correspondence between the set of currently used components and the set of currently used capabilities.

14. A method as claimed in claim 13, wherein the act of determining a correspondence includes implementing a best guess algorithm.

15. A method as claimed in claim 14, wherein a high score is assigned to a layout that exactly matches the set of currently used capabilities of the system.

16. A method as claimed in claim 14, wherein a layout containing more parameters than the parameters associated with the set of currently used capabilities of the system is assigned a score that is higher than a layout with less parameters than the parameters associated with the capabilities of the system.

17. A method as claimed in claim 13, wherein the act of determining a correspondence is implemented using a weighted system algorithm.

18. A method as claimed in claim 17, wherein predetermined weights are assigned to layout components.

19. A method as claimed in claim 18, wherein layouts are assigned weighted scores based on the weights assigned to their components.

20. A method as claimed in claim 19, wherein the at least one layout is a layout with the highest weighted score.

21. A method as claimed in claim 19, further comprising defining a layout switch threshold.

22. A method as claimed in claim 21, further comprising comparing the layout switch threshold to a weighted score of a chosen layout.

23. A method as claimed in claim 22, wherein layout switching is prevented if the weighted score of the chosen layout is less than the layout switch threshold.

24. A method as claimed in claim 13, wherein the act of determining a correspondence includes building weights for layouts according to particular system capability and environmental states.

25. A method of switching layouts in a monitoring system, each layout having one or more components, the method comprising:

determining a set of currently used external information monitoring capabilities of the system;

monitoring the system's environment to detect one or more changes in the system's environment;

after detecting one or more changes in the system's environment, reviewing a predetermined group of layouts and determining a correspondence between the components of at least one layout of the group of layouts and the set of currently used capabilities of the system; and switching from a first layout to the at least one layout if the correspondence between components of the at least one layout of the group of layouts and the set of currently used capabilities is greater than the correspondence between a set of currently used components of the first layout and the set of currently used capabilities.

26. A method as claimed in claim 25, further comprising providing a switch option interface if the correspondence between the components of the at least one layout of the group of layouts and the set of currently used capabilities is greater than the correspondence between a set of currently used components of a first layout and the currently used capabilities.

27. A method as claimed in claim 25, further comprising switching from the first layout to the at least one layout if the correspondence between the components of the at least one layout of the group of layouts and the set of currently used capabilities is greater than the correspondence between a set of currently used components of a first layout and the currently used capabilities.

28. A method as claimed in claim 25, wherein the act of determining a correspondence includes implementing a best guess algorithm.

29. A method as claimed in claim 28, wherein a high score is assigned to a layout that exactly matches the capabilities of the system.

30. A method as claimed in claim 25, wherein a layout containing more parameters than the parameters associated with the capabilities of the system is assigned a score that is higher than a layout with less parameters than the parameters associated with the capabilities of the system.

31. A method as claimed in claim 25, wherein the act of determining correspondence is implemented using a weighted system algorithm.

32. A method as claimed in claim 31, wherein predetermined weights are assigned to layout components.

33. A method as claimed in claim 32, wherein layouts are assigned weighted scores based on the weights assigned to their components.

34. A method as claimed in claim 33, wherein the at least one layout is a layout with the highest weighted score.

35. A method as claimed in claim 33, further comprising defining a layout switch threshold.

36. A method as claimed in claim 33, further comprising comparing the layout switch threshold to a weighted score of a chosen layout.

37. A method as claimed in claim 27, wherein layout switching is prevented if the weighted score of the chosen layout is less than the layout switch threshold.

38. A method as claimed in claim 25, wherein the act of determining a correspondence includes building weights for layouts according to particular system capability and environmental states.

* * * * *

UNITED STATES PATENT AND TRADEMARK OFFICE
CERTIFICATE OF CORRECTION

PATENT NO. : 6,707,476 B1
DATED : March 16, 2004
INVENTOR(S) : R. Benjamin Hochstedler It is certified that error appears in the above-identified patent and that said Letters Patent is hereby corrected as shown below:

Column 9,
Line 9, "Determining" should be -- determining --
Lines 11 and 13, "Determining" should be replaced with -- determining --
Line 16, "Monitoring" should be replaced with -- monitoring --
Line 19, "After" should be replaced with -- after --
Line 25, "Switching" should be replaced with -- switching --
Line 27, the word "on" before the word "layout" should be replaced with the word -- one --

Signed and Sealed this

Twenty-second Day of March, 2005

JON W. DUDAS
*Director of the United States Patent and Trademark Office*